(12) United States Patent
Eischeid

(10) Patent No.: US 9,648,431 B1
(45) Date of Patent: May 9, 2017

(54) ADAPTIVE AUDITORY ALERTS

(71) Applicant: ALLSCRIPTS SOFTWARE, LLC, Chicago, IL (US)

(72) Inventor: Todd Michael Eischeid, Cary, NC (US)

(73) Assignee: ALLSCRIPTS SOFTWARE, LLC, Chicago, IL (US)

(*) Notice: Subject to any disclaimer, the term of this patent is extended or adjusted under 35 U.S.C. 154(b) by 483 days.

(21) Appl. No.: 14/069,369

(22) Filed: Oct. 31, 2013

(51) Int. Cl.
*H03G 3/20* (2006.01)
*H04R 29/00* (2006.01)

(52) U.S. Cl.
CPC ..................... *H04R 29/00* (2013.01)

(58) Field of Classification Search
CPC ............ H04M 19/044; H04M 19/041; H04M 1/72569; H04M 19/04; H04M 1/6016; H04M 19/02; H04M 1/22; H04M 1/72527; H04M 1/7253; H04M 1/72558; H04M 1/72561; H04M 1/72583; H04M 2250/10; H04M 2250/22; H04M 2250/74; H04M 3/42051; H03G 3/32; H04R 1/1083; H04R 2410/05
USPC .............. 381/57, 101, 313, 107, 56, 330, 74
See application file for complete search history.

(56) References Cited

U.S. PATENT DOCUMENTS

| | | | |
|---|---|---|---|
| 7,392,066 B2* | 6/2008 | Haparnas | H04M 19/044 379/373.01 |
| 9,069,047 B2* | 6/2015 | Nallabelli | H02J 7/0047 |
| 2003/0179887 A1* | 9/2003 | Cronin | H03G 3/32 381/57 |
| 2007/0037605 A1* | 2/2007 | Logan | G08B 13/1427 455/567 |
| 2008/0043996 A1* | 2/2008 | Dolph | H04N 5/60 379/388.07 |
| 2008/0161064 A1* | 7/2008 | Lewis | H04M 19/04 455/567 |
| 2011/0135086 A1* | 6/2011 | Sun | H04M 1/6016 379/392.01 |
| 2012/0027216 A1* | 2/2012 | Tirry | H04M 1/72569 381/57 |
| 2013/0078976 A1* | 3/2013 | Naftolin | H04M 1/72569 455/418 |
| 2013/0173513 A1* | 7/2013 | Chu | G06F 9/4443 706/14 |
| 2015/0356843 A1* | 12/2015 | Yang | G08B 13/2477 340/572.1 |

* cited by examiner

*Primary Examiner* — Akelaw Teshale
(74) *Attorney, Agent, or Firm* — Tillman Wright, PLLC; Chad D. Tillman; Jeremy C. Doerre

(57) ABSTRACT

A method includes recording, at an electronic device utilizing a microphone of the electronic device, ambient noise of an environment the electronic device is disposed in; electronically analyzing, utilizing one or more processors, the recorded ambient noise of the environment to determine one or more frequency bands to avoid; dynamically adapting, based on the electronic analysis, an auditory alert to be played at the electronic device, such adaptation including frequency equalization adjustments based on the determination of one or more frequency bands to avoid; and playing, at the electronic device utilizing one or more speakers of the electronic device, the adapted auditory alert.

20 Claims, 1 Drawing Sheet

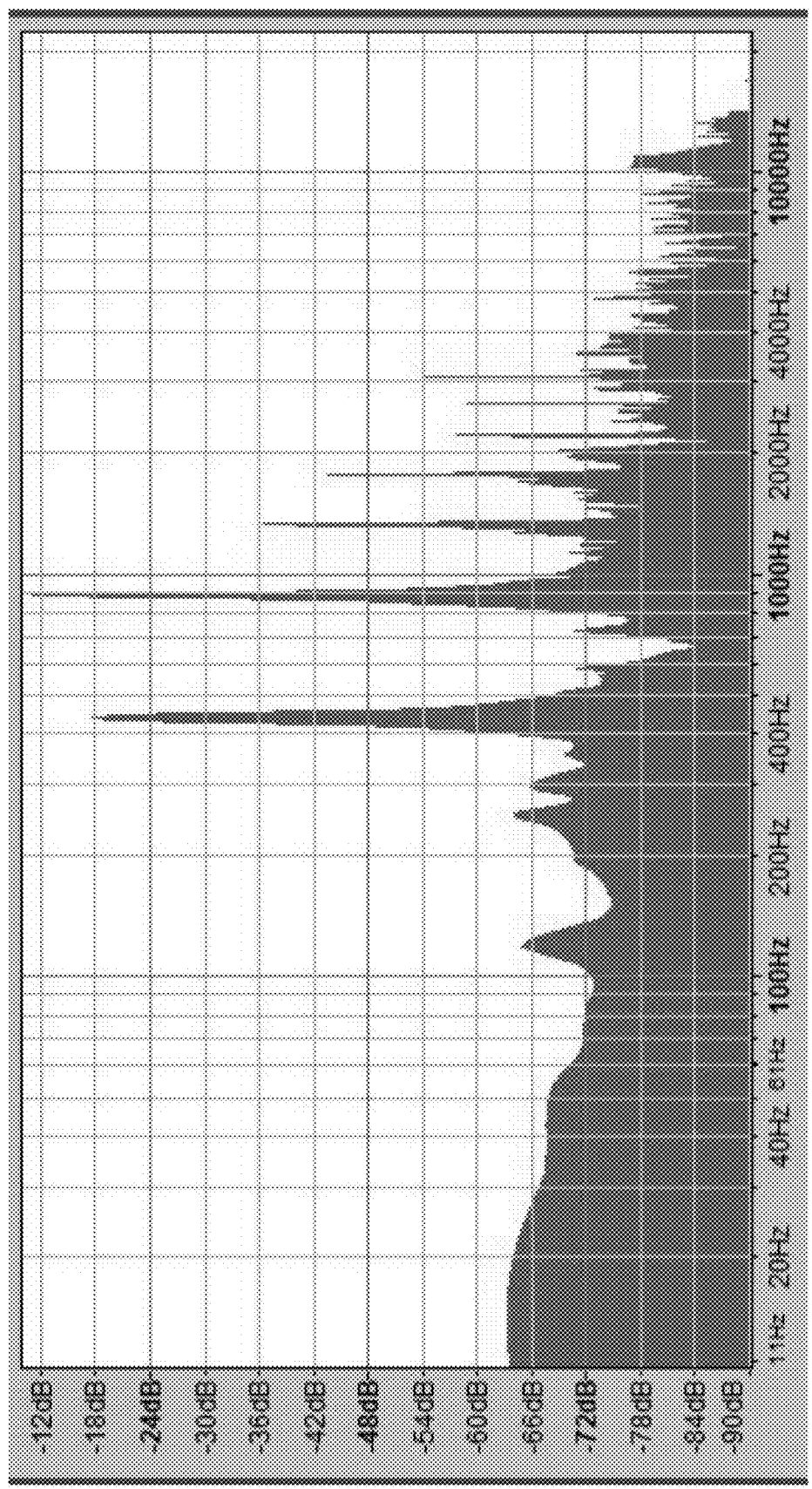

ADAPTIVE AUDITORY ALERTS

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to alerts and ringtones for an electronic device, such as cell phone or other mobile device.

Many electronic devices utilize auditory alerts to alert users to various events that may be of interest to them. Traditionally, this has included cell phone ring tones, but this also includes text alerts, weather alerts, calendar events, and other alerts, messages, and warnings.

In some environments, however, ambient noise can make hearing these auditory alerts difficult. For example, hospitals and other healthcare environments can be full of ambient noise, where multiple electronic devices such as cell phones, desk phones, wall phones, monitors, and other devices may be constantly ringing, beeping, and buzzing.

Needs exist for improvement in auditory alerts. These, and other needs, are addressed by one or more aspects of the present invention.

SUMMARY OF THE INVENTION

The present invention includes many aspects and features. Moreover, while many aspects and features relate to, and are described in, the context of mobile devices, the present invention is not limited to use only in this context, as will become apparent from the following summaries and detailed descriptions of aspects, features, and one or more embodiments of the present invention.

Accordingly, one aspect of the present invention relates to a method comprising recording, at an electronic device utilizing a microphone of the electronic device, ambient noise of an environment the electronic device is disposed in; electronically analyzing, utilizing one or more processors, the recorded ambient noise of the environment to determine one or more frequency bands to avoid; dynamically adapting, based on the electronic analysis, an auditory alert to be played at the electronic device, such adaptation including frequency equalization adjustments based on the determination of one or more frequency bands to avoid; playing, at the electronic device utilizing one or more speakers of the electronic device, the adapted auditory alert.

In a feature of this aspect, the auditory alert comprises a ringtone.

In a feature of this aspect, the auditory alert comprises a song.

In a feature of this aspect, the auditory alert comprises an alarm.

In a feature of this aspect, the electronic device comprises a cell phone.

In a feature of this aspect, the electronic device comprises a mobile phone.

In a feature of this aspect, the electronic device comprises a tablet.

In a feature of this aspect, the electronic device comprises a beeper.

In a feature of this aspect, electronically analyzing the recorded ambient noise comprises utilizing a Fast Fourier Transform.

In a feature of this aspect, electronically analyzing the recorded ambient noise comprises electronically analyzing the recorded ambient noise at the electronic device.

In a feature of this aspect, electronically analyzing the recorded ambient noise comprises electronically analyzing the recorded ambient noise at a remote server.

In a feature of this aspect, the dynamic adaptation of the auditory alert comprises adapting the attack of the auditory alert.

In a feature of this aspect, the dynamic adaptation of the auditory alert comprises adapting the decay of the auditory alert.

In a feature of this aspect, the dynamic adaptation of the auditory alert comprises modifying a volume of the auditory alert.

Another aspect relates to a method comprising recording, at a microphone disposed in an environment, ambient noise of the environment; electronically analyzing, utilizing one or more processors, the recorded ambient noise of the environment to determine one or more frequency bands to avoid; dynamically adapting, based on the electronic analysis, an auditory alert to be played at an electronic device, such adaptation including frequency equalization adjustments based on the determination of one or more frequency bands to avoid; and playing, at the electronic device utilizing one or more speakers of the electronic device, the adapted auditory alert.

In a feature of this aspect, electronically analyzing the recorded ambient noise comprises electronically analyzing the recorded ambient noise at a computing device the microphone is attached to.

In a feature of this aspect, electronically analyzing the recorded ambient noise comprises electronically analyzing the recorded ambient noise at a remote server.

Another aspect relates to a system comprising one or more non-transitory computer-readable media containing computer executable instructions for performing a method comprising recording, at an electronic device utilizing a microphone of the electronic device, ambient noise of an environment the electronic device is disposed in; electronically analyzing, utilizing one or more processors, the recorded ambient noise of the environment to determine one or more frequency bands to avoid; dynamically adapting, based on the electronic analysis, an auditory alert to be played at the electronic device, such adaptation including frequency equalization adjustments based on the determination of one or more frequency bands to avoid; and playing, at the electronic device utilizing one or more speakers of the electronic device, the adapted auditory alert.

In a feature of this aspect, electronically analyzing the recorded ambient noise comprises electronically analyzing the recorded ambient noise at the electronic device.

In a feature of this aspect, electronically analyzing the recorded ambient noise comprises electronically analyzing the recorded ambient noise at a remote server.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIG. 1 illustrates a hypothetical frequency analysis of ambient environmental noise in a particular environment.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

As noted hereinabove, in some environments, ambient noise can make it challenging to hear an auditory alert of an electronic device. Further, in some quieter environments, an auditory alert that might be appropriate for other environments might be inappropriate or grating.

In accordance with one or more preferred embodiments, a methodology is utilized to dynamically determine auditory characteristics, such as volume, sound types, and frequencies, that would be salient to a particular environment based on ambient noise for that environment. In one or more preferred implementations, this comprises determining what auditory characteristics would facilitate discerning, by a person, an auditory alert or other sound generated by the electronic device.

In one or more preferred implementations, this is accomplished by using a microphone to sample ambient noise for the environment, utilizing one or more algorithms such as a Fast Fourier Transform (FFT) in real time, and, based on the results, adapting a ring tone or other auditory alert or sound, e.g. by equalization, to make the ring tone or other auditory alert or sound stand out more with respect to the ambient noise in the environment.

For example, in a preferred implementation, a mobile device would adapt its ring tone to correspond to frequency ranges identified based on sampling of environment ambient noise to be optimal or most salient. In one or more preferred implementations, the ring tone would retain familiar aspects of the selected ring tone, so that a user would recognize the tune or sound, but equalization would change the ring tone to make the sound stand out more against the ambient sound in the environment.

In one or more preferred implementations, analysis and processing is performed entirely at a mobile electronic device, while in at least some other implementations, some or all processing may be performed remotely. In one or more preferred implementations, such processing is facilitated by communication of audio from the electronic device to one or more remote servers. In at least some other preferred implementations, audio is recorded at one or more microphones separate from an electronic device disposed in the same environment as the electronic device, and such audio is processed remotely by one or more computing devices, and results communicated to the electronic device. For example, the environment may be a hospital which has microphones placed throughout one or more areas specifically for the purpose of recording ambient noise for processing. Such processing may occur at a computing device directly connected to one or more such microphones, or at a remote computing device or server.

Implementations in which processing is offloaded from a mobile electronic device are believed to save battery life of such a mobile electronic device. Further, the constant analysis of ambient noise is generally believed to be relatively CPU intensive. Accordingly, in one or more preferred implementations, one or more remote devices make results of FFT or other analysis of environmental ambient noise available to a mobile electronic device on demand in real time, e.g. via WiFi, 3G, 4G, Bluetooth, or other connection.

In one or more preferred implementations, results of FFT or other analysis of environmental ambient noise is preferably made available to an electronic device operating system, such as a mobile device operating system, at any time, e.g. so that a ring tone can be adapted based on the frequency make-up of environmental ambient noise.

In one or more preferred implementations, a frequency spectrum, range, and/or profile of an auditory alert, ring tone, or other sound is adjusted or modified based on a frequency spectrum, range, and/or profile of, and/or frequency analysis of, ambient noise.

Although largely described herein with respect to mobile electronic devices, in one or more preferred implementations methodologies described herein are utilized with a desktop computer. It will be appreciated that methodologies described herein could be utilized with a laptop, tablet, cell phone, PDA, etc.

FIG. 1 illustrates a hypothetical frequency analysis of ambient environmental noise in a particular environment. As can be seen from this graph, there is relatively high power at frequencies around 400 Hz, 1000 Hz, and thin bands around 1500 and 1700 Hz.

Preferably, in this example, a mobile electronic device will adapt its ring tone such that it does not compete with the frequencies in the environment. Accordingly, in a preferred implementation, a ring tone would equalize its frequency spectrum to avoid 400, 1000, 1500, and 1700 Hz (and preferably multiples of these as well). It will be appreciated that this is a simplified example for illustration. The actual analysis of the environmental noise and resulting "suggested" bands by an algorithm would likely be more noisy and complex, and the effects more subtle.

In addition to frequency equalization adjustments, in one or more preferred implementations the attack and decay of a sound is adapted. A harder attack, for example, would make the sound more salient in louder environments, but would be more grating in quieter environments.

In one or more preferred implementations, sampling of ambient noise continuously occurs, or occurs at certain times, while in one or more other preferred implementations, sampling of ambient noise only occurs in response to a determination that a ring tone, auditory alert or other sound needs to be played, or in response to a determination that a ring tone, auditory alert, or other sound was not responded to by a user (e.g. a user did not answer the phone). In one or more preferred implementations, such sampling (and subsequent processing and adaptation) may only be triggered if there is a certain priority level attached to an event, communication, message, or phone call associated with the ring tone, auditory alert, or other sound.

One methodology in accordance with one or more preferred implementations for ensuring that a user will hear a ring tone is to increase the volume of a ring tone, e.g. by continually increasing the volume.

In one or more preferred implementations, volume adjustment is utilized to increase the volume of a ring tone in "loud" environments. Further, in one or more preferred implementations, volume adjustment is utilized to decrease the volume of a ring tone in "quiet" environments. Further, in one or more preferred implementations, a ring tone might be varied, e.g. a different sound or ring tone utilized, based on a "volume level" of the ambient environment.

In one or more preferred implementations, volume adjustment is utilized in combination with other adaptation of a ringtone or other auditory alert or sound. In one or more preferred implementations, an electronic device attempts to find "open" frequency bands in environmental noise, and utilize those such that the amount of volume increase would be as little as necessary.

In one or more preferred implementations, if a determination is made that a user may not be able to successfully hear a ring tone of an electronic device, and an attached severity level of an incoming call (assuming that a severity level or type of severity was available) was high, then automatic action is taken to determine another route to get in touch with a user associated with the electronic device. In one or more preferred implementations, this may include contacting a colleague in a geographically proximate location to inform the colleague that the user needs to be made aware of something.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
   (a) determining, at an electronic device disposed in a healthcare environment, that an auditory alert to be provided is associated with a high priority level;
   (b) recording, based on the determination that the auditory alert is associated with a high priority level, ambient noise in the medical environment utilizing a microphone of the electronic device;
   (c) communicating, from the electronic device to a remote server, recorded ambient noise;

(d) electronically analyzing, at the remote server, the recorded ambient noise to determine one or more frequency bands to avoid;

(e) communicating, from the remote server to the electronic device, results of the electronic analysis;

(f) dynamically adapting, based on the received results of the electronic analysis, the auditory alert to be provided at the electronic device, such adaptation including frequency equalization adjustments based on the determination of one or more frequency bands to avoid; and (g) playing, at the electronic device utilizing one or more speakers of the electronic device, the adapted auditory alert.

2. The method of claim 1, wherein the auditory alert comprises a ringtone.

3. The method of claim 1, wherein the auditory alert comprises an alarm.

4. The method of claim 1, wherein the electronic device comprises a cell phone.

5. The method of claim 1, wherein the electronic device comprises a mobile phone.

6. The method of claim 1, wherein the electronic device comprises a tablet.

7. The method of claim 1, wherein the electronic device comprises a beeper.

8. The method of claim 1, wherein electronically analyzing the recorded ambient noise comprises utilizing a Fast Fourier Transform.

9. The method of claim 1, wherein the dynamic adaptation of the auditory alert comprises adapting the attack of the auditory alert.

10. The method of claim 1, wherein the dynamic adaptation of the auditory alert comprises adapting the decay of the auditory alert.

11. The method of claim 1, wherein the dynamic adaptation of the auditory alert comprises modifying a volume of the auditory alert.

12. A method comprising:

(a) determining, at an electronic device disposed in an environment, that an auditory alert to be provided is associated with a high priority level;

(b) recording, based on the determination that the auditory alert is associated with a high priority level, ambient noise in the environment utilizing a microphone of the electronic device;

(c) communicating, from the electronic device to a remote server, recorded ambient noise;

(d) electronically analyzing, at the remote server, the recorded ambient noise to determine one or more frequency bands to avoid;

(e) communicating, from the remote server to the electronic device, results of the electronic analysis;

(f) dynamically adapting, based on the received results of the electronic analysis, the auditory alert to be provided at the electronic device, such adaptation including frequency equalization adjustments based on the determination of one or more frequency bands to avoid; and (g) playing, at the electronic device utilizing one or more speakers of the electronic device, the adapted auditory alert.

13. The method of claim 12, wherein the auditory alert comprises a ringtone.

14. The method of claim 12, wherein the auditory alert comprises an alarm.

15. The method of claim 12, wherein the electronic device comprises a mobile phone.

16. The method of claim 12, wherein the electronic device comprises a tablet.

17. The method of claim 12, wherein the electronic device comprises a beeper.

18. The method of claim 12, wherein electronically analyzing the recorded ambient noise comprises utilizing a Fast Fourier Transform.

19. The method of claim 12, wherein the dynamic adaptation of the auditory alert comprises adapting the attack of the auditory alert.

20. The method of claim 12, wherein the dynamic adaptation of the auditory alert comprises adapting the decay of the auditory alert.

* * * * *